United States Patent [19]

DeVries

[11] Patent Number: 5,248,829
[45] Date of Patent: Sep. 28, 1993

[54] PRODUCTION OF ACETYLATED AROMATIC COMPOUNDS

[75] Inventor: Robert A. DeVries, Midland, Mich.

[73] Assignee: The Dow Chemical Company, Midland, Mich.

[21] Appl. No.: 911,230

[22] Filed: Jul. 9, 1992

[51] Int. Cl.$^5$ .............................................. C07C 45/45
[52] U.S. Cl. ...................................... 568/322; 568/626
[58] Field of Search ........................ 568/222, 626, 322

[56] References Cited

U.S. PATENT DOCUMENTS

| | | | |
|---|---|---|---|
| 3,705,919 | 12/1972 | Heck | 568/626 |
| 3,767,710 | 10/1973 | Heck | 568/322 |
| 3,922,299 | 11/1975 | Heck | 260/476 R |
| 4,070,374 | 1/1978 | Chalk et al. | 568/322 |

OTHER PUBLICATIONS

Heck, *Organic Reactions*, vol. 27, 345–391 (1982).
Hallberg et al., "Palladium-Catalyzed Arylation of Methyl Vinyl Ether," *J. Org. Chem.*, vol. 46, 5414–15 (1981).
Andersson et al., "Synthesis of β-Arylvinyl Ethers by the Palladium-Catalyzed Reaction of Aryl Chlorides with Vinyl Ethers," *J. Org. Chem.*, vol. 53, 235–239 (1988).
Arai et al., "Palladium-Catalyzed Phenylation of Enol Ethers and Acetates," *J. Org. Chem.*, vol. 44, 21–23 (1979).
Andersson et al., "Chelation-Controlled, Palladium-Catalyzed Vinylic Substitution Reactions of Vinyl Ethers. 2-Arylethanal Equivalents from Aryl Halides," *J. Org. Chem.*, vol. 55, 5757–5761 (1990).
Andersson et al., "Regiochemistry of Palladium-Catalyzed Arylation Reactions of Enol Ehers. Electronic Control of Selection for α- or β-Arylation," *J. Org. Chem.*, vol. 52, 3529–3536 (1987).
Lloyd et al., "The Electrophilic Substitution of Benzocyclobutene-I," *Tetrahedron*, vol. 20, 2185–2194 (1964).
U.S. patent application Ser. No. 667,023 filed on Mar. 28, 1991 (furnished upon request).
U.S. patent application Ser. No. 676,622 filed on Mar. 28, 1991 (furnished upon request).

*Primary Examiner*—James H. Reamer
*Attorney, Agent, or Firm*—Robert M. O'Keefe

[57] ABSTRACT

This invention is a process for the production of acetylated aromatic products, including acetyl benzoeyclobutenes, in one step and in high yield. The process comprises contacting an aryl halide with an alkyl vinyl ether in the presence of a zerovalent palladium catalyst complex and a hydrogen halide acceptor in a aqueous solvent mixture containing at least about one molar equivalent of water based on moles of the aryl halide.

30 Claims, No Drawings

PRODUCTION OF ACETYLATED AROMATIC COMPOUNDS

BACKGROUND OF THE INVENTION

The invention relates to the production of acetylated aromatic compounds using a palladium catalyst.

The palladium-catalyzed vinylation of organic halides has been reviewed by Heck, *Organic Reactions*, vol. 27 (1982), beginning at page 345. Process conditions, recited at page 360, do not require the use of a solvent, although an organic amine can apparently function as a solvent. Other solvents used heretofore include acetonitrile, methanol, dimethylformamide, N-methylpyrrolidinone, and hexamethylphosphoramide.

Heck, U.S. Pat. No. 3,922,299, incorporated herein by reference, teaches that the reaction can be carried out with or without a solvent. Suggested solvents include acetonitrile, tetrahydrofuran, or excess olefin.

The Heck vinylation reaction has been used to vinylate various kinds of compounds, including the use of alkyl vinyl ethers to vinylate aryl compounds. For instance, Hallberg et al. in "Palladium-Catalyzed Arylation of Methyl Vinyl Ether," *J. Org. Chem.*, vol. 46, 5414–15 (1981), disclose that 4-nitrohalobenzenes can be reacted with methyl vinyl ether in the presence of a palladium catalyst to form a variety of products. On page 5415, Hallberg et al. disclose that the reaction of 4-iodoanisole with methyl vinyl ether in the presence of triethylamine yields an acetophenone product after work up with 10 percent aqueous hydrochloric acid. The reference is silent as to water and inorganic hydrogen halide acceptors.

In addition, Andersson et al. in "Synthesis of β-Arylvinyl Ethers by the Palladium-Catalyzed Reaction of Aryl Chlorides with Vinyl Ethers," *J. Org. Chem.*, vol. 53, 235–239 (1988), disclose reactions as defined in the title of the article. A vinylically unsaturated product is reported as the major product in every case except in the case of the reaction of anisole. The reference is silent as to water, inorganic hydrogen halide acceptors, and halogenated benzocyclobutenes. In the examples, it is noted that acid work-up produces an acetophenone from the α-isomer.

Also, Arai et al. in "Palladium-Catalyzed Phenylation of Enol Ethers and Acetates," *J. Org. Chem.*, vol. 44, 21–23 (1979), report the title reactions using triethylamine in the absence of water as a solvent. The reported products are vinyl ethers.

Andersson et al. in "Chelation-Controlled, Palladium-Catalyzed Vinylic Substitution Reactions of Vinyl Ethers. 2-Arylethanal Equivalents from Aryl Halides," *J. Org. Chem.*, vol. 55, 5757–5761 (1990), report the production of several vinyl aryl ethers as shown in Table II at page 5759. Dipotassium carbonate is disclosed as the base. Water is not added to the reaction mixture.

Additionally, Andersson et al. in "Regiochemistry of Palladium-Catalyzed Arylation Reactions of Enol Ethers. Electronic Control of Selection for α- or β-Arylation," *J. Org. Chem.*, vol. 52, 3529–3536 (1987), report arylation of vinyl alkyl ethers using palladium catalysts. α-Arylation is favored if a triphenylphosphine ligand and acetonitrile is used.

It is noted that Lloyd et al. in "The Electrophilic Substitution of Benzocyclobutene-I," *Tetrahedron*, vol. 20, 2185–2194 (1964), report that nitration, Friedal-Crafts acetylation, and hydrobromination of benzocyclobutene produce predominately ring opened products.

These references, however, do not disclose a one step process for making actyl products using Heck type chemistry.

SUMMARY OF THE INVENTION

It has surprisingly been found that the Heck-type vinylation reaction can be carried out in aqueous media, including aqueous solutions of organic solvents. It has further been found that when an organic base or an inorganic base is used in the reaction of an aryl halide with an alkyl vinyl ether, an acetylated aromatic compound is formed preferentially in one step instead of a vinylic product.

In particular it has been found that acetyl derivatives of halogenated benzocyclobutene compounds can be produced in accordance with this invention in one step. This result is significant because the conventional methods Of producing acetyl products, Friedal-Crafts chemistry for example, leads to the production of predominantly ring-opened product. The instant process, therefore, enables production in high yield of compounds heretofore difficult or impossible to prepare.

It has further been found that the type of trivalent organophosphorus compounds employed in the zerovalent palladium catalyst complex has a significant effect on product distribution.

In one respect, this invention is a process for producing an acetylated aromatic compound in one step, comprising contacting an aryl halide with a hydrogen halide acceptor and an alkyl vinyl ether in the presence of a zerovalent palladium catalyst complex comprising a palladium salt and a trivalent organophosphorus compound or a nitrogen containing heterocyclic compound in an aqueous solvent mixture containing at least about one molar equivalent of water based on moles of the aryl halide under conditions effective to produce an acetylated aromatic compound.

In another respect, this invention is a process for producing an acetylbenzocyclobutene in one step, comprising contacting a compound of the formula:

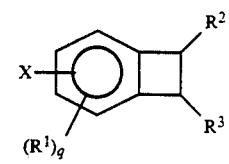

wherein X is Br or I; $R^1$ is alkyl of from 1 to 6 carbon atoms, acyloxy of from 1 to 6 carbon atoms, alkoxy of from 1 to 6 carbon atoms, trifluoroacetoxy, trifluoroalkyl, nitro, or chloro; $R^2$ and $R^3$ are independently in each occurrence hydrogen, alkyl of from 1 to 6 carbon atoms, aryl, nitro, chloro, or cyano; and q is 0, 1, 2, or 3, with a alkyl vinyl ether and a hydrogen halide acceptor in the presence of a zerovalent palladium catalyst complex comprising a palladium salt and a trivalent organophosphorus compound or a nitrogen containing heterocyclic compound in an aqueous solvent mixture of an organic solvent and water wherein the aqueous solvent mixture contains at least about one molar equivalent of water based on moles of the compound, under conditions effective to produce an acetyl derivative of said compound.

DETAILED DESCRIPTION OF THE INVENTION

The reaction between aryl halides and alkyl vinyl ethers is carried out in the presence of a zerovalent palladium catalyst complex. The catalyst complex can be added to the reaction mixture or can be formed in the reaction mixture. Examples of preformed catalyst complexes are tetrabis(triphenylphosphine)palladium (O), tris(dibenzylidene-acetone)dipalladium (O) with triphenylphosphine, and dichloro(triphenylphosphine)palladium (II).

The zerovalent palladium catalyst complex can be prepared in the reaction mixture, generally by reaction of a palladium (II) compound and a trivalent organophosphorus compound or a nitrogen containing heterocyclic compound.

Examples of useful trivalent organophosphorus compounds in the palladium catalytic complex are trimethylphosphite, triphenylphosphite, tris(o-tolyl)phosphite, tri(n-butyl)phosphine, diphenylmethylphosphine, diphenylmethoxyphosphine, triphenylphosphine, 1,2-bis(diphenylphosphino)ethane, 1,6-bis(diphenylphosphino)hexane, tris(p-trifluoromethylphenyl)phosphine, triethylphosphine, phenyldi(n-butoxy)phosphine, tris(o-methoxyphenyl)phosphine, tris(p-methoxyphenyl)phosphine, tris(p-anisyl)phosphine, tris(o-tolyl)phosphine, tris(m-tolyl)phospine, tris(p-tolyl)phosphine, tris(4-dimethylaminophenyl)phosphine, and tribenzylphosphine. Preferably, the trivalent organophosphorus compound is triphenylphosphine, tris(o-methoxyphenyl)phosphine, 1,2-bis(diphenyl-phosphino)ethane, or tris(o-tolyl)phosphine. Most preferably, the trivalent organophosphorus compound is triphenylphosphine or tris(o-tolyl)phosphine.

Examples of useful nitrogen containing heterocyclic compounds include pyridine, 1,10-phenathroline, and 2,2'-dipyridyl. Preferably, the nitrogen containing aromatic compound is 2,2'-dipyridyl.

Palladium is introduced into the reaction mixture in the form of a salt, such as palladium acetate or palladium chloride. Catalytic complexes formed from palladium (II) carboxylates, particularly Pd(II) acetate, and triaryl phosphines are particularly preferred for the practice of this invention. Most preferred zerovalent palladium catalyst complexes are those obtained from Pd(II) acetate and tris(o-tolyl)phosphine.

The molar ratio of trivalent organophosphorus compound to palladium is typically in the range from about 2:1 to about 20:1. It is preferred to operate at molar ratios in the range from about 2:1 to about 10:1, particularly when a catalyst from Pd(II) acetate and tris(o-tolyl)phosphine is used. More preferably, the molar ratio of the trivalent organophosphorous compound to palladium is from about 2:1 to about 4:1.

In the process of the present invention, the amount of palladium catalyst can vary from about 0.1 mole to 0.00001 mole per mole of aryl halide in the reaction mixture. Preferably, that catalyst level is from about 0.01 to about 0.00001 mole per mole of aryl halide.

The process of the present invention likewise produces a very high selectivity to acetylated aromatics such as acetobenzocyclobutene. For purposes of the present invention, "selectivity" is defined as the mole percentage of converted halogenated organic compound which forms an acetylated product. Preferably, the selectivity is greater than about 50 percent, more preferably greater than about 70 percent.

The process of the present invention also produces very high conversions of the aryl halide. For the purposes of this invention, "conversion" is defined as the mole percentage of aryl halide converted to product. High conversions are achieved most preferably by employing a molar ratio of trivalent organophosphorous compound to palladium is greater than about 4:1. Conversion is greater than about 50 percent. Preferably, conversion is greater than about 60 percent, more preferably greater than about 70 percent, even more preferably greater than about 85 percent, and most preferably greater than least about 90 percent.

In this invention, a hydrogen halide acceptor is employed. The hydrogen halide acceptor can be an organic hydrogen halide acceptor or an inorganic hydrogen halide acceptor. Preferably, the hydrogen halide acceptor is an inorganic hydrogen halide acceptor.

The organic hydrogen halide acceptors used in the practice of this invention are secondary or tertiary amine. Representative organic hydrogen halide acceptors include, but are not limited to, trimethylamine, triethylamine, methylethylamine, diethyl-n-butylamine, triisobutylamine, tri-n-butylamine, diisopropylamine, triisopropylamine, N,N,N',N'-tetramethylethylene diamine, N-methylcyclohexylamine, N,N-diethycyclohexylamine, N,N-diethylaniline, N,N-dimethylaniline, N-methyltoluidine, pyridine, quinoline, the lutidines, N-methylpiperidine, N-methylpyrrole, and the like. Preferred organic halogen halide acceptors are tertiary amines, particularly those represented by the formula $R_1R_2R_3N$, wherein each of $R_1$, $R_2$, and $R_3$ is selected independently from straight-chain and branched-chain alkyl of 1 to 8 carbon atoms and cycloalkyl. Most preferably, the organic hydrogen halide acceptor is triethylamine.

In the practice of this invention, the inorganic hydrogen halide acceptors are selected from salts of weak acids and strong bases or corresponding oxides or hydroxides particularly of the Group I alkali metals and Group II alkaline earth metals. Inorganic hydrogen halide acceptors include salts, oxides, and hydroxides of lithium, sodium, potassium, cesium, magnesium, calcium, strontium, and barium. Preferred inorganic hydrogen halide acceptors are selected from alkali metal hydroxides, carbonates, and carboxylates. Most preferably, the inorganic hydrogen halide acceptor is an alkali metal acetate or propionate. Most preferably, the inorganic hydrogen halide acceptors is sodium or potassium acetate.

The molar ratio of hydrogen halide acceptor to aryl halide is typically from about 1:1 to about 10:1. The molar ratio of hydrogen halide acceptor to aryl halide is preferably from about 1:1 to about 3:1. More preferably, the molar ratio of hydrogen halide acceptor to aryl halide is from about 1:1 to about 2:1.

The aqueous solvent mixture useful in the present invention contains at least about one molar equivalent of water based on the moles of aryl halide. Preferably, the aqueous solvent mixture contains at least up to about 95 percent by volume of an organic solvent. Preferred aqueous solvent mixtures contain from about 10 to about 90 percent by volume of organic solvent. Most preferably, the aqueous solvent mixtures contain from about 30 to about 70 percent by volume of organic solvent. The amount of water preferably is greater than about 50 percent by weight of the combined weight of aryl halide and alkyl vinyl ether. More preferably, the amount of water is greater than about 100 percent by weight of the combined weight of aryl halide and alkyl vinyl ether. The amount of water is selected, within these limits, so as to be sufficient to dissolve the inorganic halide salt formed during the process. Use of an amount of water sufficient to dissolve salts formed during the process greatly facilitates isolation and purification of the products. The use of an aqueous solvent mixture in the process does not adversely affect the yield or product distribution. Use of an aqueous solvent mixture containing significant amounts of water prevents formation of intractable salt accumulations in the reactor and on the stirrer. A reaction medium from which by-products do not accumulate on the walls of the reactor or stirrer permits more efficient heat transfer and better agitation than possible when salt-cake formation occurs. In some cases, phase separation into an aqueous salt-containing layer and an organic product-containing layer occurs. Separation of the reaction mixture into a two-phase system is very desirable and facilitates removing the by-product salt and isolation of the desired product from the organic phase. Organic solvents can be selected from nitriles, alcohols, ketones, linear or cyclic saturated esters, N,N-dialkylformamides, N-alkylpyrrolidinones, alkoxyalkanols, glycol ethers, dioxane, tetrahydrofuran, tetrahydropyran, or hexaalkylphosphoramides. Examples of useful nitriles are acetonitrile, propionitrile, butyronitrile, and higher aliphatic nitriles, as well as benzonitrile and tolylnitrile. A preferred nitrile solvent is acetonitrile. Alcohols which can be used include alkanols of 1 to 8 carbon atoms, including the various isomeric forms. Esters which can be used include linear or cyclic saturated esters, for example, ethyl acetate, methyl propionate, isopropyl butyrate, caprolactone and butyrolactone. Ketones which can be used include acetone, methyl ethyl ketone, methyl isopropylketone, and similar compounds. Of the various N,N-dialkylformamides which can be used, N,N-dimethylformamide is most preferred. N-methylpyrrolidione is preferred among the various N-alkylpyrrolidiones. Alkoxyalkanols suitable for use include those of up to about 10 carbon atoms. Examples of useful alkoxyalkanols are ethylene glycol monomethyl ether, propylene glycol monoethyl ether, ethylene glycol monobutyl ether, and propylene glycol monoisopropyl ether. Glycol ethers, including ethylene glycol dimethyl or diethyl ethers, corresponding propylene glycol ethers, or diethylene glycol or triethylene glycol diethers can also be used. Most preferably, the organic solvent is N,N-dimethylformamide, N-methylpyrrolidinone, or acetonitrile. Preferred aqueous solutions contain from about 10 to about 90 percent by volume of N,N-dimethylformamide or N-methylpyrrolidinone. Most preferred aqueous solutions of this invention contain from about 30 to about 70 percent by volume of N,N-dimethylformamide or N-methylpyrrolidinone.

Most preferably, the process of this invention is one wherein the aqueous solution contains from about 30 to about 70 percent by volume of N,N-dimethylformamide or N-methylpyrrolidinone and the aqueous solution is present in an amount equal to greater than about 70 percent by weight of the combined weight of aryl halide and alkyl vinyl ether.

Aryl halides useful as starting materials for the process of this invention include substituted or unsubstituted aromatic bromo and iodo compounds including both monocyclic and polycyclic aromatic halides. Aryl iodides may react in the presence of Pd(O), without a trivalent organophosphorus compound. Substituents on the aromatic ring or rings can include straight-chain and branched alkyl and alkoxy groups, nitro, cyano, hydroxy, keto, amido, carboxy, dialkylamino, sulfone groups, chloro and fluoro. Substituents on substituted aryl halides are preferably selected from alkyl of from 1 to 6 carbon atoms, alkoxy of from 1 to 6 carbon atoms, cyano, chloro, and fluoro. The preferred alkyl and alkoxy substituents can be straight-chain or branched. The aryl halide is most preferably an aryl bromide. Examples of preferred aryl halides are bromobenzene, 1-bromo-4-fluorobenzene, 1-bromo-3-fluorobenzene, 1-bromo-2-fluorobenzene, 2-bromotoluene, 3-bromotoluene, 4-bromotoluene, 4-bromobenzenecyclobutene, 4-bromoanisole, and 1-bromo-2-nitrobenzene. It has been found that when 1-bromo-2-nitrobenzene is the aryl halide, the use of an organic hydrogen halide acceptor in the zerovalent palladium catalyst complex does not produce an acetylated product. When the aryl halide is a disubstituted benzene, the substituents are preferably in either meta or para arrangement, more preferably in para arrangement.

A class of more preferred aryl halides includes bromobenzocyclobutene and iodobenzocyclobutenes, as disclosed by Gros, U.S. Pat. No. 4,759,874, incorporated herein by reference. Most preferably, the reactant is a brominated benzocyclobutene, represented by the formula:

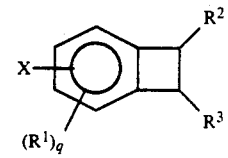

wherein X is Br or I; $R^1$ is hydrogen, alkyl of from 1 to 6 carbon atoms, acyloxy of from 1 to 6 carbon atoms, alkoxy of from 1 to 6 carbon atoms, trifluoroacetoxy, trifluoroalkyl, nitro, or chloro; $R^2$ and $R^3$ are independently in each occurrence alkyl of from 1 to 6 carbon atoms, aryl, nitro, chloro, or cyano; and q is 0, 1, 2, or 3.

Brominated benzoeyclobutenes can be prepared as recited by Liu, U.S. Pat. No. 4,822,930, incorporated herein by reference. Most preferably, 4-bromobenzoeyclobutene is the brominated benzocyclobutene used in the process of this invention.

Alkyl vinyl ethers useful as starting materials for the process of this invention include compounds of the formula $R^4R^5C=CR^6-O-R^7$ wherein $R^4$, $R^5$, and $R^6$ are independently in each occurrence hydrogen or alkyl of from 1 to 5 carbon atoms, most preferably $R^4$, $R^5$, and $R^6$ are hydrogen in each occurrence; and $R^7$ is alkyl of from 1 to 10 carbon atoms. Examples of useful alkyl vinyl ethers are methyl vinyl ether, ethyl vinyl ether, propyl vinyl ether, butyl vinyl ether, stearyl vinyl ether, and isostearyl vinyl ether. The preferred alkyl vinyl ethers are methyl vinyl ether, ethyl vinyl ether, propyl vinyl ether, and butyl vinyl ether. Most preferably, the alkyl vinyl ether is butyl vinyl ether.

The molar ratio of alkyl vinyl ether to aryl halide can be determined by routine experimentation. Generally, molar ratios from about 1:1 to about 10:1 will be preferred for the synthesis of monoadducts, more preferably from about 1:1 to about 5:1, even more preferably from about 2:1 to about 3:1, and most preferably about 3:1. When the alkyl vinyl ether is a gas, however, an excess is employed. For example, if methyl vinyl ether is used, then a 10-fold molar excess is typically employed in the process. Preferably, the molar ratio of aryl halide to gaseous alkyl vinyl ether is in the range from about 1:1 to 20:1, more preferably from about 5:1 to 15:1, most preferably about 10:1. Lower molar ratios of alkyl vinyl ether to aryl halide will be employed when higher adducts are being prepared.

It will be understood that diaromatic products (diadducts) can be readily formed by the process of this invention if a molar ratio of aryl halide to alkyl vinyl ether of greater than 1:1 is used. If diaromatic products are desired, it is preferable to employ a molar ratio of aryl halide to alkyl vinyl ether of greater than about 2:1. Higher molar ratios can be employed, although it is preferable to not exceed a molar ratio of about 10:1.

The temperature at which the process of this invention is typically performed is a temperature in the range from about room temperature to the temperature at which the starting materials or products decompose or polymerize. It has been found that heating under reflux, generally at a temperature in the range from about 75° C. to about 125° C., provides a reasonable reaction rate. The temperature conditions required for a given set of reactants and diluent can readily be ascertained by routine experimentation.

The compounds prepared by the process of this invention can be purified by distillation, chromatography, or crystallization as may be apparent to a person skilled in the art.

The compounds prepared by the process of this invention have a variety of utilities.

The following examples are given to illustrate the invention and should not be construed as limiting its scope. All parts and percentages are by weight unless otherwise indicated.

GENERAL PROCEDURE FOR THE COUPLING REACTIONS

The following general procedure was used in a series of runs. A flask is loaded with solvent (37.5 ml; 12.5 ml water, 25.0 ml of DMF), aryl bromide (0.0546 mole), butyl vinyl ether (0.0546 mole), potassium acetate or triethylamine (0.1092 mole), palladium acetate (0.00055 mole), tris(o-tolyl)phosphine (0.0022 mole). The aryl bromide/butyl vinyl ether/potassium acetate/palladium acetate/tris(o-tolyl)phosphine molar ratio is 100:100:200:1:4. The flask is equipped with a condenser, thermowell, stir bar, nitrogen inlet, and bubbler. The apparatus is heated by a heating mantel attached to temperature controller, high limit, and timer. The contents of the vessel are purged with nitrogen several minutes before heating. Samples can be taken by cooling below reflux and removing by micropipet. The final product is isolated by cooling to room temperature, pouring out the liquid phase, and then adding about 50 ml of water to dissolve any salts which precipitate during the reaction.

The flask contents are poured into an eight ounce bottle and the flask is rinsed with 50 ml of water and 50 ml of methylene chloride. The organic layer is isolated in a separatory funnel and is washed with an additional 50 ml of water. The crude product is filtered over a small bed of silica gel on a filter assembly.

The products are analyzed by conventional methods using capillary gas chromatography. Analyses are run on a sample after 24 to 27 hours. The results are reported in the following Tables. In the Tables, "AN" denotes acetonitrile, "DMF" denotes N,N-dimethylformamide, "TEA" denotes triethylamine, "KOAc" denotes potassium acetate, "ArBr" denotes aryl bromide, "BVE:ArBr" denotes the molar ratio of butyl vinyl ether to the aryl bromide, "GC Area %" denotes the percentage area of the indicated product or by-product analyzed by gas chromatography, "β-aryl ether adducts" denotes the sum total GC area percent of the β-aryl ether adducts.

EXAMPLE 1

Coupling Reactions of Butyl Vinyl Ether and 1-Bromo-4-fluorobenzene

A series of runs with varying butyl vinyl ether proportions are run according to the General Procedure using 1-bromo-4-fluorobenzene as the aryl bromide. In these runs, the solvent is water/DMF as in the General Procedure. The results are reported in Table 1.

TABLE 1

| Aryl Bromide | Base | Solvent | BVE:ArBr | GC Area % | | |
|---|---|---|---|---|---|---|
| | | | | Acetyl Product | α-aryl ether adducts | β-aryl ether adducts |
| 1-bromo-4-fluoro-benzene | KOAc | DMF/H$_2$O | 1 | 35.24 | 0.13 | 19.91 |
| 1-bromo-4-fluoro-benzene | KOAc | DMF/H$_2$O | 1 | 24.66 | 0.17 | 19.9 |
| 1-bromo-4-fluoro-benzene | KOAc | DMF/H$_2$O | 2 | 37.30 | — | 46.67 |
| 1-bromo-4-fluoro-benzene | KOAc | DMF/H$_2$O | 3 | 40.30 | — | 39.22 |
| 1-bromo-2-fluoro-benzene | KOAc | DMF/H$_2$O | 3 | 21.08 | 22.89 | 21.05 |
| 1-bromo-3-fluoro-benzene | KOAc | DMF/H$_2$O | 3 | 27.40 | — | 55.45 |
| 1-bromo-3-fluoro-benzene | TEA | DMF/H$_2$O | 1 | 23.77 | 1.94 | 38.66 |
| 1-bromo-3-fluoro-benzene | TEA | DMF/H$_2$O | 3 | 7.11 | 45.49 | 39.13 |
| 1-bromo-3-fluoro-benzene | TEA | DMF/H$_2$O | 2 | 13.71 | 33.09 | 43.07 |
| 1-bromo-2-fluoro-benzene | TEA | DMF/H$_2$O | 3 | 1.21 | 66.46 | 21.67 |
| 1-bromo-3-fluoro-benzene | TEA | DMF/H$_2$O | 3 | 1.18 | 37.49 | 52.87 |

Comparative Experiment 1

(Not an Embodiment of the Invention)

The procedure of Example 1 is repeated except the solvent is anhydrous. The results are shown in Table 2.

TABLE 2

| Aryl Bromide | Base | Solvent | BVE:ArBr | Acetyl Product | α-aryl ether adducts | β-aryl ether adducts |
|---|---|---|---|---|---|---|
| 1-bromo-4-fluoro-benzene | TEA | AN | 1 | 0.71 | 48.50 | 32.6 |
| 1-bromo-4-fluoro-benzene | TEA | DMF | 3 | 5.08 | 32.32 | 36.12 |
| 1-bromo-4-fluoro-benzene | TEA | AN | 3 | 1.00 | 58.40 | 31.56 |

EXAMPLE 2

Coupling Reactions of Butyl Vinyl Ether and 2-, 3-, or 4-bromotoluene

The General Procedure is repeated using 2-, 3-, or 4-bromotoluene as the aryl bromide. The results are shown in Table 3.

TABLE 3

| Aryl Bromide | Base | Solvent | BVE:ArBr | Acetyl Product | α-aryl ether adducts | β-aryl ether adducts |
|---|---|---|---|---|---|---|
| 2-bromotoluene | KOAc | DMF/H$_2$O | 3 | 44.37 | 0.25 | 37.74 |
| 3-bromotoluene | KOAc | DMF/H$_2$O | 3 | 27.82 | — | 56.03 |
| 4-bromotoluene | KOAc | DMF/H$_2$O | 3 | 44.26 | 0.07 | 38.46 |
| 2-bromotoluene | TEA | DMF/H$_2$O | 3 | 2.75 | 57.78 | 32.56 |
| 3-bromotoluene | TEA | DMF/H$_2$O | 3 | 10.13 | 26.66 | 51.9 |
| 4-bromotoluene | TEA | DMF/H$_2$O | 3 | 16.50 | 26.00 | 48.03 |

EXAMPLE 3

Coupling Reactions of Butyl Vinyl Ether and Bromobenzocyclobutene

The General Procedure is repeated except the aryl bromide is 4-bromobenzenocyclobutene. The results are reported in Table 4.

TABLE 4

| Aryl Bromide | Base | Solvent | BVE:ArBr | Acetyl Product | α-aryl ether adducts | β-aryl ether adducts |
|---|---|---|---|---|---|---|
| 4-bromobenzene-cyclobutene | KOAc | DMF/H$_2$O | 3 | 45.41 | — | 41.93 |
| 4-bromobenzene-cyclobutene | KOAc | DMF/H$_2$O | 3 | 39.20 | — | 45.20 |
| 4-bromobenzene-cyclobutene | KOAc | DMF/H$_2$O | 3 | 33.44 | — | 34.90 |
| 4-bromobenzene-cyclobutene | TEA | DMF/H$_2$O | 3 | 30.03 | 6.07 | 51.87 |

Comparative Experiment 2

(Not an Embodiment of the Invention)

The procedure of Example 3 is repeated except the solvent is anhydrous. The results are reported in Table 5.

TABLE 5

| Aryl Bromide | Base | Solvent | BVE:ArBr | Acetyl Product | α-aryl ether adducts | β-aryl ether adducts |
|---|---|---|---|---|---|---|
| 4-bromobenzene-cyclobutene | TEA | DMF/H$_2$O | 3 | — | 50.80 | 37.00 |
| 4-bromobenzene-cyclobutene | KOAc | DMF/H$_2$O | 3 | 0.37 | 41.62 | 33.60 |

EXAMPLE 4

Coupling Reactions of Butyl Vinyl Ether and Bromoanisole

The General Procedure is repeated using bromoanisole as the aryl bromide. The results are reported in Table 6.

TABLE 6

| Aryl Bromide | Base | Solvent | BVE:ArBr | Acetyl Product | GC Area % α-aryl ether adducts | β-aryl ether adducts |
|---|---|---|---|---|---|---|
| 4-bromoanisole | KOAc | DMF/H$_2$O | 3 | 55.11 | — | 31.71 |
| 4-iodoanisole | TEA | DMF/H$_2$O | 3 | 38.5 | — | 34.7 |
| 4-bromoanisole | TEA | DMF/H$_2$O | 3 | 41.95 | — | 46.03 |

Comparative Experiment 3
(Not an Embodiment of the Invention)

The procedure of Example 4 is repeated except the solvent is anhydrous. The results are shown in Table 7.

TABLE 7

| Aryl Bromide | Base | Solvent | BVE:ArBr | Acetyl Product | GC Area % α-aryl ether adducts | β-aryl ether adducts |
|---|---|---|---|---|---|---|
| 4-iodoanisole | TEA | DMF | 3 | 4.0 | 66.7 | 15.5 |

EXAMPLE 5

Coupling Reactions of But Ether and Bromobenzene

The General Procedure is repeated using bromobenzene as the aryl bromide. The results are reported in Table 8.

TABLE 8

| Aryl Bromide | Base | Solvent | BVE:ArBr | Acetyl Product | GC Area % α-aryl ether adducts | β-aryl ether adducts |
|---|---|---|---|---|---|---|
| bromobenzene | KOAc | DMF/H$_2$O | 3 | 37.64 | — | 53.94 |
| bromobenzene | TEA | DMF/H$_2$O | 3 | 9.23 | 25.66 | 48.26 |

EXAMPLE 6

Coupling Reactions of Bromonitrobenzene

The General Procedure is repeated except the aryl bromide is bromonitrobenzene. The results are reported in Table 9.

TABLE 9

| Aryl Bromide | Base | Solvent | BVE:ArBr | Acetyl Product | GC Area % α-aryl ether adducts | β-aryl ether adducts |
|---|---|---|---|---|---|---|
| 1-bromo-2-nitrobenzene | KOAc | DMF/H$_2$O | 3 | 21.09 | 45.36 | 4.29 |
| 1-bromo-2-nitrobenzene | KOAc | DMF/H$_2$O | 3 | 6.29 | 17.32 | 62.34 |

EXAMPLE 7

Coupling Reactions of Vinyl Butyl Ether and Bromobenzocyclobutene Using Various Ligands The General Procedure is repeated using 4-bromobenzocyclobutene as the aryl bromide and using several ligands. A molar ratio of BVE to 4-bromobenzocyclobutene is 3:1. The results are shown in Table 10.

TABLE 10

| Phosphine Ligand | Acetyl | E-trans | Z-cis | Ratio E/Z | Total Beta | Alpha Select. (%) | Beta Select. (%) | Conv. (%) | Acetyl Yield (%) |
|---|---|---|---|---|---|---|---|---|---|
| tris(o-tolyl)phosphine | 45.41 | 22.57 | 19.36 | 1.17 | 41.93 | 52 | 48 | 100.0 | 45.4 |
| triphenylphosphine | 33.44 | 26.30 | 8.60 | 3.00 | 34.90 | 49 | 51 | 89.5 | 37.4 |
| tris(p-tolyl)phosphine | 24.86 | 19.17 | 5.37 | 3.57 | 24.54 | 51 | 49 | 78.8 | 31.5 |
| tris(p-methoxyphenyl)phosphine | 30.75 | 25.64 | 7.59 | 3.38 | 33.23 | 48 | 52 | 87.5 | 35.1 |
| tris(o-methoxyphenyl)phosphine | 51.24 | 6.14 | 2.70 | 2.27 | 8.84 | 85 | 15 | 81.4 | 62.9 |
| 1,2-bis(diphenylphosphino)ethane | 31.68 | 15.83 | 4.93 | 3.21 | 20.76 | 60 | 40 | 79.6 | 39.8 |
| tris(m-tolyl)phosphine | 25.76 | 20.10 | 5.77 | 3.48 | 25.87 | 50 | 50 | 81.5 | 31.6 |
| 1,6- | 17.76 | 12.45 | 3.69 | 3.37 | 16.14 | 52 | 48 | 56.6 | 31.3 |

TABLE 10-continued

| Phosphine Ligand | Acetyl | E-trans | Z-cis | Ratio E/Z | Total Beta | Alpha Select. (%) | Beta Select. (%) | Conv. (%) | Acetyl Yield (%) |
|---|---|---|---|---|---|---|---|---|---|
| bis(diphenylphosphino)hexane | | | | | | | | | |
| 1,10-phenanthroline | 6.39 | 0.18 | 0.26 | 0.69 | 0.44 | 94? | 6? | 20.1 | 31.8 |
| 2,2'-dipyridyl | 13.67 | 0.54 | 0.46 | 1.17 | 1.00 | 93? | 7? | 31.6 | 43.2 |
| tris(p-fluorophenyl)phosphine | 24.73 | 16.62 | 5.74 | 2.90 | 22.36 | 53 | 47 | 74.2 | 33.3 |
| tris(p-trifluoromethylphenyl)phosphine | 24.92 | 17.98 | 7.24 | 2.48 | 25.22 | 50 | 50 | 80.6 | 30.9 |
| triphenylphosphite | 9.60 | 5.88 | 2.27 | 2.59 | 8.15 | 54 | 46 | 30.8 | 31.1 |
| tris(4-dimethylaminophenyl)phosphine | 10.39 | 13.65 | 4.87 | 2.80 | 18.52 | 36 | 64 | 51.8 | 20.0 |
| tris(n-butyl)phosphine | 1.89 | 2.97 | 0.00 | — | 2.97 | 39 | 61 | 9.2 | 20.5 |
| tribenzylphosphine | 19.52 | 13.87 | 4.91 | 2.82 | 18.78 | 51 | 49 | 66.4 | 29.4 |

What is claimed is:

1. A process for producing an acetylated aromatic compound in one step, comprising contacting an aryl halide, wherein the aryl halide can be substituted or unsubstituted and when substituted the substituent is alkyl of from 1 to 6 carbon atoms, alkoxy of from 1 to 6 carbon atoms, nitro, cyano, hydroxy, amido, ketone, carboxy, dialkylamine, or sulfone, with an inorganic hydrogen halide acceptor or an organic hydrogen halide acceptor, wherein the inorganic hydrogen halide acceptor is a salt, an oxide, or a hydroxide of lithium, sodium, potassium, cesium, magnesium, calcium, strontium, or barium, wherein the organic hydrogen halide acceptor is of the formula $R_1R_2R_3N$ wherein each or $R_1$, $R_2$, and $R_3$ is independently in each occurrence a straight-chain alkyl, branched-chain alkyl, or cycloalkyl of 1 to 8 carbon atoms, and an alkyl vinyl ether of the formula $R^4R^5C=CR^6-O-R^7$ wherein $R^4$, $R^5$, and $R^6$ are independently in each occurrence hydrogen or alkyl of from 1 to 5 carbon atoms and $R^7$ is alkyl of from 1 to 10 carbon atoms in the presence of a zerovalent palladium catalyst complex comprising a palladium salt and a trivalent organophosphorus compound or a nitrogen containing heterocyclic compound selected from the group consisting of pyridine, 1,10-phenathroline, and 2,2'-dipyridyl in an aqueous solvent mixture containing at least about one molar equivalent of water based on the moles of the aryl halide under conditions effective to produce an acetylated aromatic compound.

2. The process of claim 1 wherein the aqueous solvent mixture contains up to about 95 percent by volume of an organic solvent.

3. The process of claim 1 wherein the trivalent organophosphorus compound is tripenylphosphine, tris(o-methoxyphenyl)phosphine, bis(dophenylphosphino)ethane, or tris-(o-tolyl)phosphine or wherein the nitrogen containing heterocyclic compound is 2,2'-dipyridyl.

4. The process of claim 1 wherein the organic solvent is N,N-dimethylformamide, N-methylpyrrolidione, acetonitrile, or mixtures thereof.

5. The process of claim 1 wherein the aqueous solvent mixture contains from about 10 to about 90 percent by volume of the organic solvent.

6. The process of claim 3 wherein the aqueous solvent mixture contains from about 30 to about 70 percent by volume of the organic solvent.

7. The process of claim 1 wherein the palladium salt is a palladium (II) carboxylate.

8. The process of claim 1 wherein the palladium salt is palladium acetate.

9. The process of claim 1 wherein the selectivity is greater than about 50 percent.

10. The process of claim 1 wherein the hydrogen halide acceptor is an inorganic hydrogen halide acceptor.

11. The process of claim 10 wherein the inorganic hydrogen halide acceptor is sodium acetate or potassium acetate.

12. The process of claim 1 wherein the aryl halide is bromo or iodo benzene substituted by straight-chain or branched alkyl and alkoxy groups of from 1 to 6 carbon atoms, nitro, cyano, hydroxy, keto, amido, carboxy, dialkylamino, sulfone groups, chloro, and fluoro.

13. The process of claim 12 wherein the aryl halide is bromobenzene, 1-bromo-4-fluorobenzene, 1-bromo-3-fluorobenzene, 1-bromo-2-fluorobenzene, 2-bromotoluene, 3-bromotoluene, 4-bromotoluene, 4-bromobenzenecyclobutene, 4-bromoanisole, and 1-bromo-2-nitrobenzene.

14. The process of claim 12 wherein the aryl halide is meta or para substituted.

15. The process of claim 1 wherein the alkyl vinyl ether is methyl vinyl ether, ethyl vinyl ether, propyl vinyl ether, butyl vinyl ether, stearyl vinyl ether, or isostearyl vinyl ether.

16. The process of claim 1 wherein the temperature is from about 75° C. and 125° C.

17. A process for producing an acetylbenzocyclobutene in one step, comprising contacting a compound of the formula:

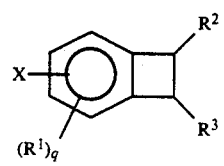

wherein X is Br or I; $R^1$ is hydrogen, alkyl of from 1 to 6 carbon atoms, acyloxy of from 1 to 6 carbon atoms, alkoxy of from 1 to 6 carbon atoms, trifluoroacetoxy, trifluoroalkyl, nitro, or chloro; $R^2$ and $R^3$ are independently in each occurrence hydrogen, alkyl of from 1 to 6 carbon atoms, aryl, nitro, chloro, or cyano; and q is 0, 1, 2, or 3, with an alkyl vinyl ether of the formula $R^4R^5C=CR^6-O-R^7$ wherein $R^4$, $R^5$, and $R^6$ are independently in each occurrence hydrogen or alkyl of from 1 to 5 carbon atoms and $R^7$ is alkyl of from 1 to 10 carbon atoms and an inorganic hydrogen halide acceptor or an organic hydrogen halide acceptor, wherein the inorganic hydrogen halide acceptor is a salt, an oxide, or a hydroxide of lithium, sodium potassium, cesium, magnesium, calcium, strontium, or barium, wherein the organic hydrogen halide acceptor is of the formula $R_1R_2R_3N$ wherein each or $R_1$, $R_2$, and $R_3$ is independently in each occurrence a straight-chain alkyl, branched-chain alkyl, or cycloalkyl of 1 to 8 carbon atoms, in the presence of a zerovalent palladium catalyst complex comprising a palladium salt and a trivalent organophosphorus compound or a nitrogen containing heterocyclic compound selected from the group consisting of pyridine, 1,10-phenathroline, and 2,2'-dipyridyl in an aqueous solvent mixture of an organic solvent and water wherein the aqueous solvent mixture contains at least about one molar equivalent of water based on moles of the compound, under conditions effective to produce an acetyl derivative of said compound.

18. The process of claim 17 wherein the aqueous solvent mixture contains up to about 95 percent by volume of organic solvent.

19. The process of claim 17 wherein the trivalent organophosphorus compound is triphenylphosphine, tris(o-methoxyphenyl)phosphine, bis(diphenylphosphino)ethane, or tris-(o-tolyl)phosphine or wherein the nitrogen containing heterocyclic compound is 2,2'-dipyridyl.

20. The process of claim 17 wherein the organic solvent is N,N-dimethylformamide, N-methylpyrrolidione, acetonitrile, or mixtures thereof.

21. The process of claim 17 wherein the aqueous solvent mixture contains from about 10 to about 90 percent by volume of the organic solvent.

22. The process of claim 17 wherein the aqueous solvent mixture contains from about 30 to about 70 percent by volume of the organic solvent.

23. The process of claim 17 wherein the palladium salt is a palladium (II) carboxylate.

24. The process of claim 23 wherein the palladium salt is palladium acetate.

25. The process of claim 17 wherein the selectivity is greater than about 50 percent.

26. The process of claim 17 wherein the hydrogen halide acceptor is an inorganic hydrogen halide acceptor.

27. The process of claim 26 wherein the inorganic hydrogen halide acceptor is sodium acetate or potassium acetate.

28. The process of claim 17 wherein the compound is 4-bromo-benzocyclobutene.

29. The process of claim 17 wherein the alkyl vinyl ether is methyl vinyl ether, ethyl vinyl ether, propyl vinyl ether, butyl vinyl ether, stearyl vinyl ether, or isostearyl vinyl ether.

30. The process of claim 17 wherein the temperature is from about 75° C. to about 125° C.

* * * * *